(12) United States Patent 
Richardson

(10) Patent No.: US 6,965,836 B2
(45) Date of Patent: Nov. 15, 2005

(54) METHOD AND APPARATUS FOR TWO DIMENSIONAL SURFACE PROPERTY ANALYSIS BASED ON BOUNDARY MEASUREMENT

(75) Inventor: John G. Richardson, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 16 days.

(21) Appl. No.: 10/828,633

(22) Filed: Apr. 19, 2004

(65) Prior Publication Data

US 2005/0234664 A1  Oct. 20, 2005

(51) Int. Cl.$^7$ .......................... G01R 13/02; G06F 19/00
(52) U.S. Cl. ...................................................... 702/57
(58) Field of Search .............................. 702/65, 57, 58, 702/108, 127, 133; 324/525, 691, 693, 696

(56) References Cited

U.S. PATENT DOCUMENTS

| | | | |
|---|---|---|---|
| 3,697,864 A * | 10/1972 | Runge .......................... | 324/368 |
| 4,814,690 A | 3/1989 | Melcher et al. | |
| 5,165,794 A | 11/1992 | Ortiz | |
| 5,381,333 A | 1/1995 | Isaacson et al. | |
| 5,911,158 A | 6/1999 | Henderson et al. | |
| 6,088,655 A * | 7/2000 | Daily et al. ..................... | 702/7 |
| 6,501,984 B1 | 12/2002 | Church et al. | |
| 2003/0183015 A1 * | 10/2003 | Richardson et al. .......... | 73/772 |
| 2003/0196485 A1 | 10/2003 | Schoor et al. | |

OTHER PUBLICATIONS

Rerkratn et al., "Electrical Impedance Tomography System using 3D Finite Algorithm," IEEE 0-7803-6355-8/00/, 2000, I-499-I-502.
Baglio et al, "Automatic Measurement System for the Estimation of Surface Resistivity Distribution," IEEE 0-7803-6646-08/01, 2001 pp. 902-905.

* cited by examiner

Primary Examiner—Michael Nghiem
Assistant Examiner—Demetrius Pretlow
(74) Attorney, Agent, or Firm—Trask Britt, P.C.

(57) ABSTRACT

An apparatus and method for determining properties of a conductive film is disclosed. A plurality of probe locations selected around a periphery of the conductive film define a plurality of measurement lines between each probe location and all other probe locations. Electrical resistance may be measured along each of the measurement lines. A lumped parameter model may be developed based on the measured values of electrical resistance. The lumped parameter model may be used to estimate resistivity at one or more selected locations encompassed by the plurality of probe locations. The resistivity may be extrapolated to other physical properties if the conductive film includes a correlation between resistivity and the other physical properties. A profile of the conductive film may be developed by determining resistivity at a plurality of locations. The conductive film may be applied to a structure such that resistivity may be estimated and profiled for the structure's surface.

62 Claims, 3 Drawing Sheets

FIG. 4A  FIG. 4B

METHOD AND APPARATUS FOR TWO DIMENSIONAL SURFACE PROPERTY ANALYSIS BASED ON BOUNDARY MEASUREMENT

CONTRACTUAL ORIGIN OF THE INVENTION

This invention was made with United States Government support under Contract No. DE-AC07-99ID13727 awarded by the United States Department of Energy. The United States Government has certain rights in the invention.

BACKGROUND OF THE INVENTION

1. Field of the Invention

The present invention relates to nondestructive material evaluation and, in particular, to a method for characterizing and evaluating integrity and physical properties of electrically conducting material structures.

2. Description of Related Art

Structures and the materials comprising those structures are often evaluated for integrity and other physical properties using a variety of nondestructive evaluation techniques. These techniques include thermographic, optical, acoustic, radiographic (e.g., x-ray), and electromagnetic procedures.

Electrical impedance measurement and analysis of structures and their surfaces is of particular interest because often, the impedance characteristics of a surface may correlate to other physical phenomena, such as strain on the surface, thermal characteristics of the surface, photosensitivity of the surface, and physical integrity of the surface.

In the area of strain measurements, conventional foil type electrical strain gauges are often used to measure deformation of a structure or deformation of the surface of a structure. However, strain gauges typically cover only a small area of the structure. As a result, strain gauges are typically used in specific areas of a structure where a problem, such as stress concentration or orientation of concern, is likely to exist or where measurements are desired due to the geometry and configuration of the structure at that specific area. The cost and effort required to cover a significant surface area of a structure with resistance strain gauges may be prohibitive. Additionally, a technique using multiple strain gauges would likely require the presence of conductive, such as wire, leads extending to each strain gauge distributed across the surface to be observed, which may be impractical in many applications.

Techniques exist for measuring and modeling physical properties of the surface of a structure, when the surface is electrically conductive. See, for example, U.S. Pat. No. 5,165,794 to Ortiz for a Method For The Thermal Characterization, Visualization, and Integrity Evaluation of Conducting Material Samples or Complex Structures. However, like a strain gauge implementation, the Ortiz patent requires wire leads attached to measurement points distributed throughout the surface of the structure, which may be impractical in many applications.

Many techniques, such as electrical impedance tomography, exist for measuring and analyzing electrical impedance characteristics of an object by only placing measurement probes around the periphery of the object. Unfortunately, these solutions are typically volumetric solutions requiring the object to be somewhat conductive throughout the volume of the object. Additionally, tomography techniques are generally used to characterize resistivity through the object as a whole in three dimensions, or at least of a cross section through the object. Thus, for analysis concerned with the surface characteristics of an object, these electrical impedance tomography techniques are generally inadequate.

A method and apparatus is needed to nondestructively measure and analyze electrical resistance parameters of a conductive film, or a conductive surface of a structure, while only requiring the use of measurement points around the periphery of the conductive film or conductive surface. Additionally, a method and apparatus is needed to extrapolate the electrical resistive parameters of the structure to other physical properties such as thermal characteristics of the structure at the surface, photosensitivity of the surface of the structure, strain on the structure surface, and physical integrity of the structure surface.

BRIEF SUMMARY OF THE INVENTION

One embodiment of the present invention includes a method for determining physical properties of a conductive film. A plurality of probe locations may be selected around a periphery of the conductive film. A plurality of measurement lines may be defined as the line segments that may be drawn between each probe location and all other probe locations in the plurality of probe locations. Electrical resistance may be measured along each of the plurality of measurement lines. Based on the measured electrical resistance values, a lumped parameter resistance model may be developed with lumped resistance values existing along each measurement line. Using linear algebra, the lumped parameter resistance model may be determined based on the measured resistance values. Using the lumped parameter resistance model, electrical resistivity may be modeled at any selected location encompassed by the plurality of probe locations. If the conductive film includes a correlation between electrical resistivity and another physical property, the correlation may be used to extrapolate from the modeled resistivity at the selected location to the desired physical property at the same selected location. A profile of the conductive film may be developed by determining the resistivity and other physical properties at a plurality of selected locations.

In another embodiment of the present invention, the conductive film to be analyzed may be applied to the surface of a structure. Once the conductive film is applied, the conductive film may be analyzed as described to arrive at resistivity or other physical property at the selected location. An electrical resistivity value may be estimated at a selected location on the conductive film encompassed by the plurality of probe locations. The structure may be an essentially two-dimensional object on which the surface is to be analyzed. Additionally, the structure may be a three-dimensional structure, wherein the conductive film covers a surface or multiple surfaces of the structure. Additionally, the surface(s) covered may be curved. In other words, the surface(s) may be nonplanar.

In another embodiment of the present invention, the previously described analysis may be performed on a structure that already incorporates the conductive film.

Yet another embodiment of the present invention includes a system configured for determining surface properties of a structure bearing a conductive film over a surface of the structure. The system includes a plurality of probes adapted for of measuring an electrical resistance when the plurality of probes are placed at the plurality of probe locations around the periphery of the conductive film. The plurality of probes connect to a signal controller. The signal controller may be configured to select any pair of the plurality of probes at any given time for measuring the resistance values along all the measurement lines. A signal sampler, operably coupled to the signal controller, may be configured to sample the electrical resistance between the currently selected pair of the plurality of probes. The sample may be digitized and sent to a suitably programmed processor, which may then be used to perform the method described above to determine resistivity or other physical properties at a selected location. By analyzing a plurality of selected locations, the system may be used to develop a profile of the resistivity or other physical properties across the surface of the conductive film or surface of the structure.

BRIEF DESCRIPTION OF THE DRAWINGS

In the drawings, which illustrate what is currently considered to be the best mode for carrying out the invention:

FIG. 4A is a diagram of a rectangular conductive film indicating probe locations and measurement lines on the conductive film;

FIG. 4B is a representation of a cylindrical structure for acceptance of a conductive film;

DETAILED DESCRIPTION OF THE INVENTION

Figure 1:
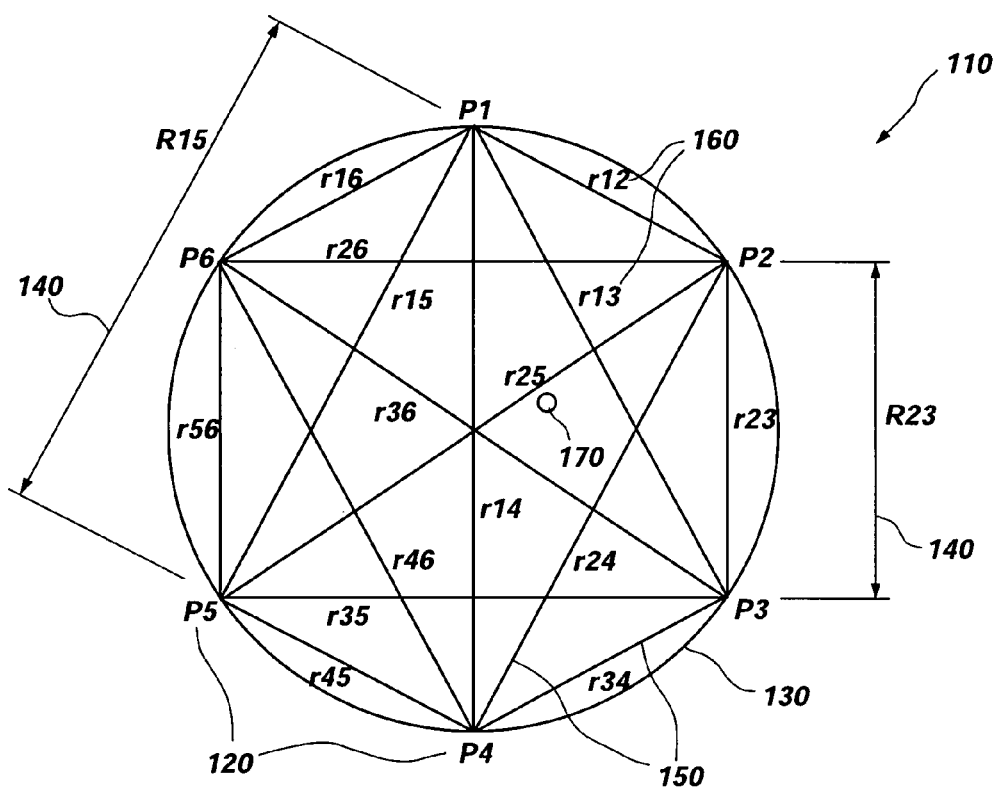
FIG. 1 is a diagram of a circular conductive film indicating probe locations and measurement lines on the conductive film.

An exemplary embodiment of the present invention includes a method of analyzing resistance, or other physical properties, of a conductive film 110. As shown in FIG. 1, a plurality of probe locations 120 may be selected around the periphery 130 of the conductive film 110. The probe locations 120 may be selected in a manner allowing one or more areas of interest, where property analysis is desired to be encompassed within a boundary defined by line segments extending between each of the adjacent probe locations 120. For example, in FIG. 1, with N(six) probe locations 120, the boundary is defined by six line segments (i.e., line segment P1–P2, line segment P2–P3, line segment P3–P4, line segment P4–P5, line segment P5–P6, and line segment P6–P1).

As a result of selection of the probe locations 120, an analysis mesh is defined by line segments, also referred to as measurement lines 150, between each probe location and all other probe locations 120 in the plurality of probe locations 120. In general, N probe locations 120 define a total of N*N measurement lines 150 between the probe points at which discrete resistance measurements may be taken. Obviously, this total of N*N measurements includes measurements of resistivity between a probe location and itself, which is a point rather than a line segment, and therefore need not be measured. Additionally, a resistance measurement along, for example, line segment P1–P5 will be the same when measured from P1 to P5 and from P5 to P1. So, even though it is convenient to discuss, and populate a matrix with, N*N discrete measurement values, only (N*(N–1))/2 actual discrete measurements are required.

A mesh, in the context of this analysis, refers to the resultant set of lines as defined above. It is important to note that this mesh does not necessarily refer to the intersections between lines as may be thought of in the case of a typical mesh. The analysis method used in the present invention does not rely on determining property values at intersection points of measurement lines 150. Rather, it relies on measurements around the periphery 130 combined with analysis and estimation using these periphery measurements without requiring determination of properties at internal intersection points.

Resistance measurements are obtained along each of the measurement lines 150 to arrive at a set of measured resistance values 140. These measured resistance values 140 are shown in the figures with a capital R followed by the points defining the line segment along which the measurement is taken. Resistance may be measured using various techniques well known in the art. For example, using a simple Ohmmeter to directly measure resistance, placing a specific voltage potential between two probe locations 120 and measuring the resultant current, and causing a specific current to flow between any two probe locations 120 and measuring the resultant voltage drop.

Having collected the set of measured resistance values 140, a lumped parameter resistance model 160 may be determined for the analysis mesh. The measured values of resistance form an N×N matrix $[R_{ij}]$ of measured electrical resistances 140. The overall sheet resistance of the conductive film 110 may be characterized as a set of lumped parameter resistance models 160. If the lumped parameter resistance models 160 are defined between the same probe locations 120 as for the measured values of resistance, a matrix of $[r_{ij}]$ lumped parameter resistance models 160 is defined. A linear transformation, well known in the art, may be developed to define the relationship between the lumped parameter resistance models 160 and the measured resistance values 140. This relationship may be defined as a transformation matrix of coefficients [F] based on the physical geometries of the conductive sheet and the relative placement of the probe locations 120. Therefore, we can write in general that the measured resistance values 140 are a function of the lumped parameter resistance models 160. This may be written in matrix form as:

$$[R_{ij}] = F[r_{ij}]$$

i=1 to N
j=1 to N

As a result there are N equations and N unknowns and one may solve for the lumped parameter resistance models 160 using linear algebra and inverting the coefficient matrix to arrive at:

$$[r_{ij}] = F^{-1}[R_{ij}]$$

With a solution for the lumped parameter resistance models 160, we have a model to determine resistivity at any point on the conductive film 110 encompassed by the probe locations 120. This is performed with a weighted average interpolation.

The interpolation process occurs by first creating a bounded region of the conductive film 110 encompassing a selected location 170. The bounded region is defined by selecting three probe locations 120 with three measurement lines 150 between the probe locations 120 defining a triangle encompassing the selected location 170. The lumped parameter resistance models 160 for each of the three measurement lines 150 are used in the interpolation. The model assumes the resistance per unit length is substantially constant along a measurement line 150 such that the resistivity is substantially the same at any point along the measurement line 150.

Figure 2:
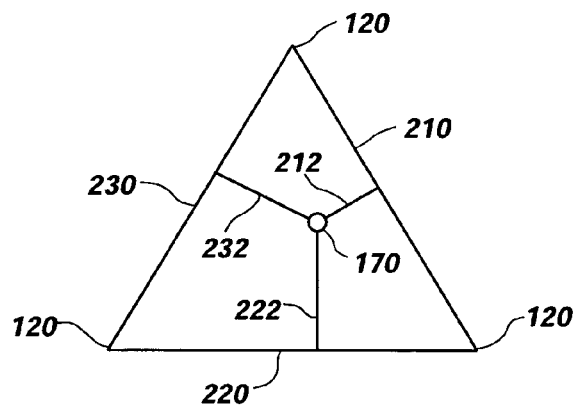
FIG. 2 is a diagram indicating measurement lines and various distances used calculating weighted averages used in determining resistivity at a selected location.

To create the weightings, an orthogonal distance is determined from each of the three selected measurement lines 150 to the selected location 170. For example, in FIG. 2, a first measurement line 210 between probe locations 120 has a first orthogonal distance 212 (also referred to as $d_{za}$) to the selected location 170. A second measurement line 220 between probe locations 120 has a second orthogonal distance 222 (also referred to as $d_{zb}$) to the selected location 170. Finally, a third measurement line 230 between probe locations 120 has a third orthogonal distance 232 (also referred to as $d_{zc}$) to the selected location 170. The weighted contribution of a given measurement line 150 is a function of the orthogonal distance from the selected location 170 to the measurement line 150 relative to the sum of orthogonal distances for all three measurement lines. For example, the weighted contribution for the first measurement line 210 is defined as:

$$1 - d_{za}/(d_{za} + d_{zb} + d_{zc})$$

As may be seen and readily appreciated, if the selected location 170 is very close to the measurement line 150, the orthogonal distance for that line will be small, resulting in a large weighted contribution.

The final weighted average is computed as the resistivity ($\rho_a$, $\rho_b$, $\rho_c$) of each measurement line (210, 220, 230) multiplied by its corresponding weighted contribution, as defined by:

$$\rho_z = \rho_c\{1 - d_{zc}/(d_{za} + d_{zb} + d_{zc})\} + \rho_b\{1 - d_{zb}/(d_{za} + d_{zb} + d_{zc})\} + \rho_a\{1 - d_{za}/(d_{za} + d_{zb} + d_{zc})\}$$

A plurality of selected locations 170 may be analyzed to develop a profile of resistivity across the entire surface of the conductive film 110. Additionally, as described below, the profile may be developed for other physical properties that may be correlative to the resistivity profile.

Selective timing of the measurement and analysis is also contemplated within the scope of the invention. It may, for example, be desirable to trigger the measurement and analysis after an event which may, for example, be indicated by outputs of one or more sensors. For example, if the invention is included on an aircraft wing, it may be desirable to trigger a new measurement and develop a new profile after an accelerometer output reaches certain parameters. For a storage tank, a new measurement may be taken and a new profile developed when stored material within the tank is at a certain level. Pressure and temperature measurements may also be used to trigger a measurement and analysis cycle. Alternatively, or in addition to triggering responsive to a sensed event, measurements in accordance with the present invention may be taken at various times, for example, perhaps periodically, and combined with the profiling to develop a time-varying profile of electrical resistivity or other physical property.

Figure 3:
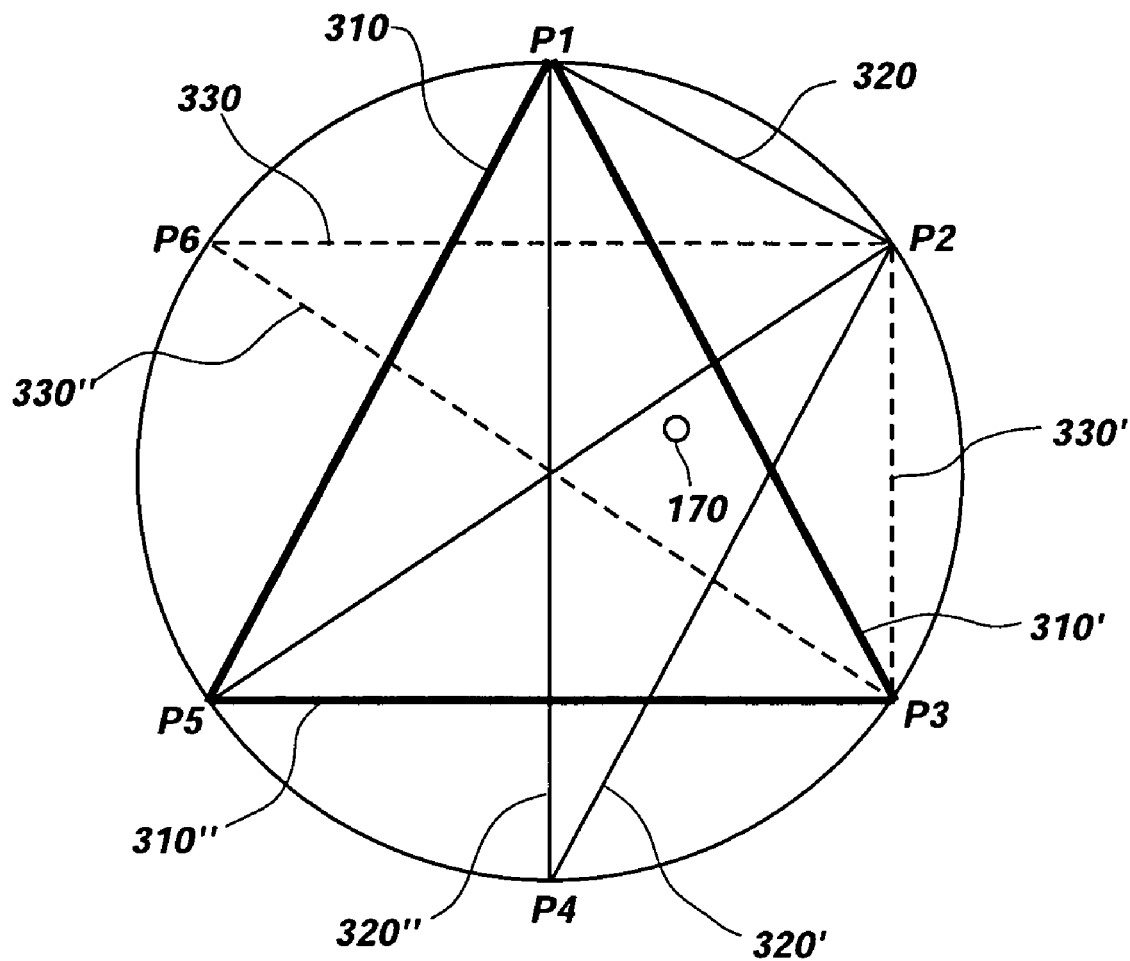
FIG. 3 is a diagram depicting various analysis triangles that may be used in a weighted average analysis to determine resistivity at a selected location.

For most geometries comprising a relatively large number of probe locations 120, many different bounding triangles may be defined. As an example, FIG. 3 shows three different bounding triangles encompassing the selected location 170. A first triangle is defined by the first triangle measurement lines (310, 310', 310") between probe locations P1, P3, and P5; a second triangle is defined by the second triangle measurement lines (320, 320', 320") between probe locations P1, P2, and P4; and a third triangle is defined by the third triangle measurement lines (330, 330', 330") between probe locations P2, P3, and P6. Other possible bounding triangles are not shown. A more accurate overall weighted average may be possible by combining the weighted average from multiple bounding triangles. For example, all possible bounding triangles may be combined to arrive at a more accurate overall weighted average. Alternatively, an analysis of most likely candidates may be used to identify bounding triangles that may produce the most accurate results. For example, an analysis may select only bounding triangles with a combined orthogonal distance (i.e., $d_{za} + d_{zb} + d_{zc}$) below a predetermined threshold. This would emphasize those bounding triangles comprised of measurement lines 150 closest to the selected location 170.

An advantage of the present invention is redundancy provided by multiple, noncoincident bounding triangles. As explained above, and referring to FIG. 1, with a relatively large number of probe locations 120, multiple bounding triangles are likely for any given selected location 170. This is an advantage because there may be anomalies in the conductive film 110. For example, discontinuities may develop due to, as examples only, punctures, tears, cracks, or other damage to the surface of the structure. The present invention may be used to locate these anomalous areas. However, if a measurement line 150 crosses the anomalous area, the measured electrical resistivity value, and as a result the lumped parameter resistance model 160, for that measurement line 150 may be inaccurate. The present invention may compensate for possibly inaccurate measured resistance values 140 by removing the suspect measurement line 150 from the analysis. Typically, other redundant bounding triangles will exist after removal of the suspect measurement line 150. These remaining bounding triangles may be used in the weighted average analysis to develop a profile for locating the anomalous area.

The present invention may be embodied in a variety of physical configurations. In the simplest exemplary embodiments, the conductive film 110 may be a simple geometric shape, such as, for example, the circle of FIG. 1, a square, a triangle, or an ellipse. However, the actual two-dimensional shape of the film may take on virtually any shape. For irregular shapes, probe locations 120 may need to be chosen at irregular intervals around the periphery 130 to obtain the necessary coverage of the analysis mesh.

Figure 4C:
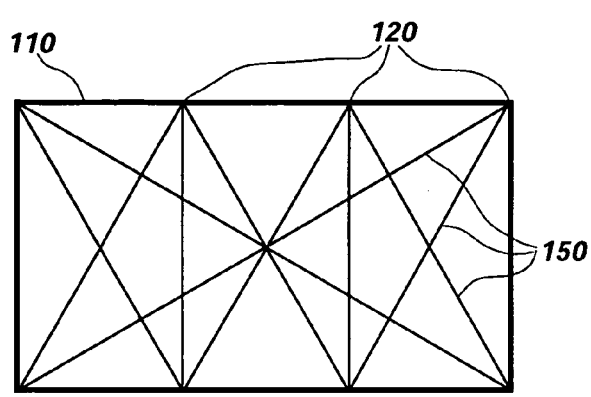
FIG. 4C is a representation of the cylindrical structure with the conductive film applied to the surface of the structure.
Figure 4C:
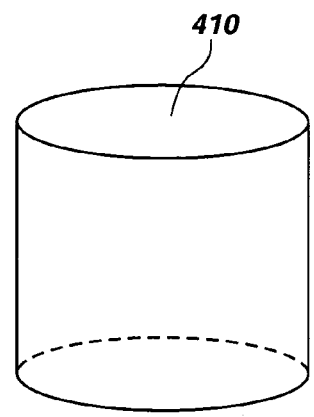
Figure 4C:
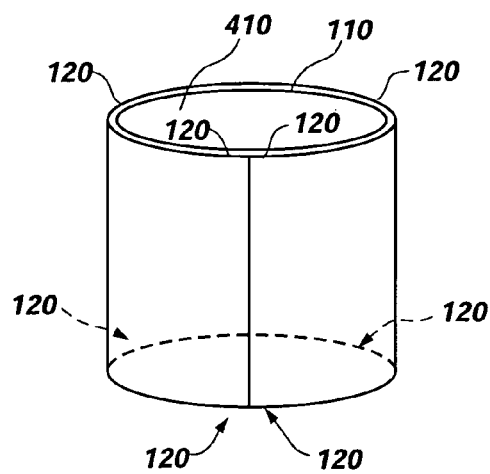

While the analysis is two dimensional, and the conductive film 10 may be applied to an essentially two-dimensional structure, the analysis is not limited to two-dimensional structures. Rather, when used on a three-dimensional structure the analysis is of the surface properties of the structure, as opposed to the volumetric properties of the structure. The film may be applied to curved surfaces or across a plurality of surfaces comprising the three-dimensional structure. Thus, the conductive film 110 may be attached to various structures such as, by way of example only, storage vessels, ship hulls, aircraft wings, spacecraft wings, turbine blades, body armor on military combat tanks, personal body armor, and vehicle axles. FIGS. 4A–4C illustrate one exemplary three-dimensional structure 410. FIG. 4A illustrates a rectangular conductive film 110 including probe locations 120 and measurement lines 150. FIG. 4B illustrates a cylindrical storage vessel 410. FIG. 4C illustrates the conductive film 110 attached around the perimeter of the cylindrical storage vessel 410. As can be seen, the probe locations 120 are still around the periphery 130 of the cylindrical storage vessel 410 at points along the top circular surface and the bottom circular surface. This configuration allows detection of anomalies around the cylindrical portion of the cylindrical storage vessel 410. Additionally, depending on the type of conductive film 110 used, this configuration may enable detection and profiling of other physical properties such as stress characteristics, thermal characteristics, and photosensitivity.

It should be noted that the analysis may not be as effective when using periphery measurements on a structure or film with a very large aspect ratio. For example, the cylindrical storage vessel illustrated in FIGS. 4B and 4C, has a large aspect ration when the cylindrical storage vessel is very tall, with a small circumference. If probe locations are only at the top and bottom circles, the analysis triangles become significantly extended in one direction and small along at least one of the triangle legs creating diminished resolution along the long axis. If intermediate probe locations may be placed along the long axis of the structure or film, this large aspect ratio disparity may be alleviated.

A variety of conductive films 110 may be employed in the present invention. As long as the conductive film 110 has adequate electrical conductivity for the analysis described above, the conductive film 110 may be adapted to be sensitive to other physical properties. For example, the conductive film 110 may be made of a metal having a correlation between resistivity and deformation, similar to that of metals used in strain gauges. A conductive film 10 having this correlation to deformation may be used to profile stresses across the conductive film 10 and surface of the structure attached thereto. As another example, the conductive film 10 may comprise a metal film similar to that used for metal film temperature transducers, such as platinum, enabling profiling of temperature across the conductive film 10 and surface of the structure attached thereto. A temperature profile may also be extrapolated to related parameters such as thermal transmissivity of portions of the underlying structure Yet another example is a photosensitive material, such as for example, cadmium sulfide. Using a photosensitive material enables profiling various intensities of light impinging on the conductive film 10. Additionally, a photosensitive material may be targeted at specific radiation wavelengths.

The mode of attaching the conductive film 10 to the surface of the structure also may vary. Attachment methods may vary depending on the material used for the conductive film 110 and physical properties of interest. For example, if a deformation of stress at various points on a structure is desired, the conductive film 110 may be applied using an adhesive that enables the conductive film 10 to contiguously deform, compress, or stretch with the underlying surface of the structure. On the other hand, if surface temperature of the structure is the desired property, the conductive film 10 may be attached in a different manner. For thermal applications, it is more important to ensure adequate thermal conductivity between the material to be measured and the conductive film 10, rather than the distributed physical attachment required for stress measurements.

The conductive film 110 may not necessarily comprise a prefabricated sheet adhered to the structure in some fashion. Instead, the conductive film 10 may be applied to the structure using a method such as spraying on the film, the spraying technique varying with the material of the film. For example, a metallic coating may be thermally sprayed on a surface. Thus, a powder of a material such as alumina or copper may be sprayed at a high temperature, using so-called plasma spraying techniques, onto a structure creating a thin, continuous, and evenly distributed conductive film 10. For extremely fine control of film properties, chemical vapor deposition (CVD), plasma enhanced chemical vapor deposition (PECVD), or even atomic layer deposition (ALD) may be employed to deposit a variety of materials.

Figure 5:
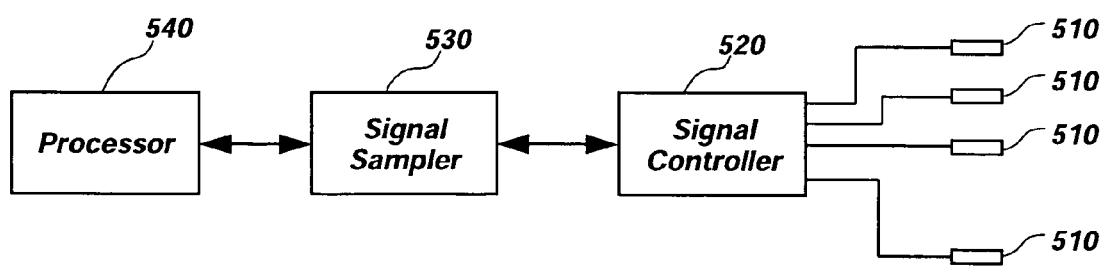
FIG. 5 is a block diagram of a system for analyzing surface properties of a structure bearing a conductive film.

As shown in FIG. 5, the present invention also includes a system configured for determining surface properties of a structure bearing the conductive film 10 over the structure's surface. This system includes a plurality of probes 510 adapted for measuring electrical resistance 140. Each of the plurality of probes 510 connect to a signal controller 520. The signal controller 520 typically may be an analog multiplexer configured for selecting any two of the plurality of probes 510 for making a resistance measurement across a selected measurement line 150 (see, for example, FIG. 1). After making a resistance measurement, the analog multiplexer may be switched to a different pair of probes 510 to make a measurement on a different measurement line 150. A signal sampler 530, connected to the signal controller 520, may be used to sample a value on the currently selected pair of probes 510 and convert the sample from an analog signal to a digital signal. A suitably programmed processor 540, connected to the signal sampler 530, may be used to receive the digital signal and performs the analysis described above. The processor may be any computer, microcontroller, microprocessor, digital signal processor, or custom circuit, configured for performing the required analysis.

Although this invention has been described with reference to particular embodiments, the invention is not limited to these described embodiments. Rather, the invention is limited only by the appended claims, which include within their scope all equivalent devices or methods that operate according to the principles of the invention as described.

What is claimed is:

1. A method for determining properties of a conductive film, comprising:
   selecting a plurality of probe locations proximate a periphery of the conductive film;
   measuring electrical resistance along a plurality of measurement lines, the plurality of measurement lines comprising line segments extending between each probe location and at least some other probe locations in the plurality of probe locations;
   analyzing the measured electrical resistances to determine a lumped parameter resistance model along the plurality of measurement lines; and
   estimating an electrical resistivity value at a selected location on the conductive film encompassed by measurement lines extending between at least three of the plurality of probe locations.

2. The method of claim 1, further comprising extrapolating the electrical resistivity value at the selected location to another physical property correlative with the electrical resistivity value.

3. The method of claim 2, wherein the other physical property is selected from the group consisting of a thermal property, strain, photosensitivity, and physical anomalies.

4. The method of claim 1, further comprising initiating the measuring, analyzing and estimating in response to an event.

5. The method of claim 1, further comprising repeating the estimating for a plurality of selected locations to develop a resistivity profile across the conductive film.

6. The method of claim 5, further comprising extrapolating the resistivity profile to a profile of another physical property correlative with the resistivity profile.

7. The method of claim 6, wherein the another physical property is selected from the group consisting of a thermal property, strain, photosensitivity, and physical anomalies.

8. The method of claim 1, further comprising repeating the measuring, analyzing, and estimating for a plurality of selected locations and at a plurality of times to develop a time varying resistivity profile across the conductive film.

9. The method of claim 8, further comprising extrapolating the time varying resistivity profile to a time varying profile of another physical property correlative with the time varying resistivity profile.

10. The method of claim 9, wherein the another physical property is selected from the group consisting of a thermal property, strain, photosensitivity, and physical anomalies.

11. The method of claim 1, wherein the estimating further comprises performing a weighted average of the lumped parameter resistance model associated with each of three measurement lines defining a triangle encompassing the selected location to determine the electrical resistivity value, wherein the weighted average is related to orthogonal distances from the selected location to each of the three measurement lines defining the triangle.

12. The method of claim 1, wherein the estimating further comprises:
    performing a weighted average of the lumped parameter resistance model associated with each of three measurement lines defining a triangle encompassing the selected location to determine a first electrical resistivity value, wherein the weighted average is related to orthogonal distances from the selected location to each of the three measurement lines defining the triangle;
    performing a at least one additional weighted average of the lumped parameter resistance model associated with each of three other measurement lines, at least two of which are different than measurement lines of the three measurement lines, defining an additional triangle encompassing the selected location to determine at least one additional electrical resistivity value, wherein the weighted average is related to orthogonal distances from the selected location to each of the three other measurement lines defining the additional triangle; and
    combining the first electrical resistivity value and the at least one additional electrical resistivity value to determine the electrical resistivity value.

13. The method of claim 1, further comprising removing at least one measured electrical resistance from consideration in the analyzing.

14. The method of claim 13, further comprising estimating when the at least one measured electrical resistance to be removed is anomalous.

15. The method of claim 1, wherein the conductive film is applied on a surface of a structure.

16. The method of claim 15, wherein the surface of the structure comprises a nonplanar surface in three dimensions.

17. A method for determining surface properties of a structure, comprising:
    applying an electrically conductive film to a surface of the structure;
    selecting a plurality of probe locations proximate a periphery of the conductive film;
    measuring electrical resistance along a plurality of measurement lines, the plurality of measurement lines comprising line segments extending between each probe location and at least some other probe locations in the plurality of probe locations;
    analyzing the measured electrical resistances to determine a lumped parameter resistance model along the plurality of measurement lines; and
    estimating an electrical resistivity value at a selected location on the conductive film encompassed by measurement lines extending between at least three of the plurality of probe locations.

18. The method of claim 17, wherein the applying is effected by at least one of adhering, forming, spraying, thermally spraying, chemical vapor deposition, plasma enhanced chemical vapor deposition or atomic layer deposition.

19. The method of claim 17, further comprising extrapolating the electrical resistivity value at the selected location to another physical property correlative with the electrical resistivity value.

20. The method of claim 19, wherein the another physical property is selected from the group consisting of a thermal property, strain, photosensitivity, and physical anomalies.

21. The method of claim 17, further comprising initiating the measuring, analyzing and estimating in response to an event.

22. The method of claim 17, further comprising repeating the estimating for a plurality of selected locations to develop a resistivity profile across the conductive film.

23. The method of claim 22, further comprising extrapolating the resistivity profile to a profile of another physical property correlative with the resistivity profile.

24. The method of claim 23, wherein the another physical property is selected from the group consisting of a thermal property, strain, photosensitivity, and physical anomalies.

25. The method of claim 17, further comprising repeating the measuring, analyzing, and estimating for a plurality of selected locations and at a plurality of times to develop a time varying resistivity profile across the conductive film.

26. The method of claim 25, further comprising extrapolating the time varying resistivity profile to a time varying profile of another physical property correlative with the time varying resistivity profile.

27. The method of claim 26, wherein the another physical property is selected from the group consisting of a thermal property, strain, photosensitivity, and physical anomalies.

28. The method of claim 17, wherein the estimating further comprises performing a weighted average of the lumped parameter resistance model associated with each of three measurement lines defining a triangle encompassing the selected location to determine the electrical resistivity value, wherein the weighted average is related to orthogonal distances from the selected location to each of the three measurement lines defining the triangle.

29. The method of claim 17, wherein the estimating further comprises:
    performing a weighted average of the lumped parameter resistance model associated with each of three measurement lines defining a triangle encompassing the selected location to determine a first electrical resistivity value, wherein the weighted average is related to orthogonal distances from the selected location to each of the three measurement lines defining the triangle;
    performing a at least one additional weighted average of the lumped parameter resistance model associated with each of three other measurement lines, at least two of which are different than measurement lines of the three measurement lines, defining an additional triangle encompassing the selected location to determine at least one additional electrical resistivity value, wherein the weighted average is related to orthogonal distances from the selected location to each of the three other measurement lines defining the additional triangle; and
    combining the first electrical resistivity value and the at least one additional electrical resistivity value to determine the electrical resistivity value.

30. The method of claim 17, further comprising removing at least one measured electrical resistance from consideration in the analyzing.

31. The method of claim 30, further comprising estimating when the at least one measured electrical resistance to be removed is anomalous.

32. The method of claim 17, wherein the surface of the structure comprises a nonplanar surface in three dimensions.

33. A method for determining surface properties of a structure bearing an electrically conductive film over a surface of the structure, comprising:
    selecting a plurality of probe locations proximate a periphery of the conductive film;
    measuring electrical resistance along a plurality of measurement lines, the plurality of measurement lines comprising line segments extending between each probe location and at least some other probe locations in the plurality of probe locations;
    analyzing the measured electrical resistances to determine a lumped parameter resistance model along the plurality of measurement lines; and
    estimating an electrical resistivity value at a selected location on the conductive film encompassed by measurement lines extending between at least three of the plurality of probe locations.

34. The method of claim 33, further comprising extrapolating the electrical resistivity value at the selected location to another physical property correlative with the electrical resistivity value.

35. The method of claim 34, wherein the another physical property is selected from the group consisting of a thermal property, strain, photosensitivity, and physical anomalies.

36. The method of claim 33, further comprising initiating the measuring, analyzing and estimating in response to an event.

37. The method of claim 33, further comprising repeating the estimating for a plurality of selected locations to develop a resistivity profile across the conductive film.

38. The method of claim 37, further comprising extrapolating the resistivity profile to a profile of another physical property correlative with the resistivity profile.

39. The method of claim 38, wherein the another physical property is selected from the group consisting of a thermal property, strain, photosensitivity, and physical anomalies.

40. The method of claim 33, further comprising repeating the measuring, analyzing, and estimating for a plurality of selected locations and at a plurality of times to develop a time varying resistivity profile across the conductive film.

41. The method of claim 40, further comprising extrapolating the time varying resistivity profile to a time varying profile of another physical property correlative with the time varying resistivity profile.

42. The method of claim 41, wherein the another physical property is selected from the group consisting of a thermal property, strain, photosensitivity, and physical anomalies.

43. The method of claim 33, wherein the estimating further comprises performing a weighted average of the lumped parameter resistance model associated with each of three measurement lines defining a triangle encompassing the selected location to determine the electrical resistivity value, wherein the weighted average is related to orthogonal distances from the selected location to each of the three measurement lines defining the triangle.

44. The method of claim 33, wherein the estimating further comprises:
    performing a weighted average of the lumped parameter resistance model associated with each of three measurement lines defining a triangle encompassing the selected location to determine a first electrical resistivity value, wherein the weighted average is related to orthogonal distances from the selected location to each of the three measurement lines defining the triangle;
    performing a at least one additional weighted average of the lumped parameter resistance model associated with each of three other measurement lines, at least two of which are different than measurement lines of the three measurement lines, defining an additional triangle encompassing the selected location to determine at least one additional electrical resistivity value, wherein the weighted average is related to orthogonal distances from the selected location to each of the three other measurement lines defining the additional triangle; and
    combining the first electrical resistivity value and the at least one additional electrical resistivity value to determine the electrical resistivity value.

45. The method of claim 33, further comprising removing at least one measured electrical resistance from consideration in the analyzing.

46. The method of claim 45, further comprising estimating when the at least one measured electrical resistance to be removed is anomalous.

47. The method of claim 33, wherein the surface of the structure comprises a nonplanar surface in three dimensions.

48. A system configured for determining surface properties of a structure bearing an electrically conductive film over a surface thereof, comprising:
    a plurality of probes adapted for measuring an electrical resistance when placed at a plurality of probe locations proximate a periphery of the conductive film;
    a signal controller operably coupled to each of the plurality of probes and configured for selecting at least one pair of probes of the plurality of probes at any given time;
    a signal sampler operably coupled to the signal controller and configured for sampling the electrical resistance between probes of the selected at least one pair of probes; and
    a processor operably coupled to the signal sampler and configured for:
    analyzing a plurality of sampled electrical resistances to determine a lumped parameter resistance model; and
    estimating an electrical resistivity value at a selected location on the conductive film encompassed by at measurement lines extending between least three of the plurality of probe locations.

49. The system of claim 48, wherein the processor is further configured for extrapolating the electrical resistivity value at the selected location to another physical property correlative with the electrical resistivity value.

50. The system of claim 49, wherein the another physical property is selected from the group consisting of a thermal property, strain, photosensitivity, and physical anomalies.

51. The system of claim 48, wherein the processor is further configured for initiating the measuring, analyzing and estimating in response to an event.

52. The system of claim 48, wherein the processor is further configured for repeating the estimating for a plurality of selected locations to develop a resistivity profile across the conductive film.

53. The system of claim 52, wherein the processor is further configured for extrapolating the resistivity profile to a profile of another physical property correlative with the resistivity profile.

54. The system of claim 53, wherein the another physical property is selected from the group consisting of a thermal property, strain, photosensitivity, and physical anomalies.

55. The system of claim 48, wherein the processor is further configured for repeating the measuring, analyzing, and estimating for a plurality of selected locations and at a plurality of times to develop a time varying resistivity profile across the conductive film.

56. The system of claim 55, wherein the processor is further configured for extrapolating the time varying resistivity profile to a time varying profile of another physical property correlative with the time varying resistivity profile.

57. The system of claim 56, wherein the another physical property is selected from the group consisting of a thermal property, strain, photosensitivity, and physical anomalies.

58. The system of claim 48, wherein the estimating further comprises performing a weighted average of the lumped parameter resistance model associated with each of three measurement lines defining a triangle encompassing the selected location to determine the electrical resistivity value, wherein the weighted average is related to orthogonal distances from the selected location to each of the three measurement lines defining the triangle.

59. The system of claim 48, wherein the estimating further comprises:
performing a weighted average of the lumped parameter resistance model associated with each of three measurement lines defining a triangle encompassing the selected location to determine a first electrical resistivity value, wherein the weighted average is related to orthogonal distances from the selected location to each of the three measurement lines defining the triangle;
performing a at least one additional weighted average of the lumped parameter resistance model associated with each of three other measurement lines, at least two of which are different than measurement lines of the three measurement lines, defining an additional triangle encompassing the selected location to determine at least one additional electrical resistivity value, wherein the weighted average is related to orthogonal distances from the selected location to each of the three other measurement lines defining the additional triangle; and
combining the first electrical resistivity value and the at least one additional electrical resistivity value to determine the electrical resistivity value.

60. The system of claim 48, wherein the processor is further configured for removing at least one measured electrical resistance from consideration in the analyzing.

61. The system of claim 60, wherein the processor is further configured for estimating when the at least one measured electrical resistance to be removed is anomalous.

62. The system of claim 48, wherein the surface of the structure comprises a nonplanar surface in three dimensions.

* * * * *